(12) United States Patent
Leschinsky

(10) Patent No.: US 6,306,145 B1
(45) Date of Patent: *Oct. 23, 2001

(54) REDUCED DIAMETER STENT/GRAFT DEPLOYMENT CATHETER

(75) Inventor: Boris Leschinsky, Waldwick, NJ (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/541,215

(22) Filed: Apr. 3, 2000

Related U.S. Application Data

(63) Continuation of application No. 09/006,113, filed on Jan. 13, 1998, now Pat. No. 6,074,398.

(51) Int. Cl.⁷ ..................................................... A61F 11/00
(52) U.S. Cl. ............................................................. 606/108
(58) Field of Search .................................... 606/108, 191, 606/194, 192, 195, 159; 604/89, 82, 85, 90

(56) References Cited

U.S. PATENT DOCUMENTS

| | | |
|---|---|---|
| 3,835,855 * | 9/1974 | Barr, Jr. ........................ 128/218 M |
| 5,669,920 | 9/1997 | Conley et al. . |
| 5,700,269 | 12/1997 | Pinchuk et al. . |
| 5,772,669 | 6/1998 | Vrba . |
| 5,776,140 | 7/1998 | Cottone . |
| 5,792,144 | 8/1998 | Fischell et al. . |
| 5,810,837 | 9/1998 | Hofmann et al. . |
| 5,843,092 | 12/1998 | Heller et al. . |

* cited by examiner

Primary Examiner—Henry J. Recla
Assistant Examiner—Vy Q. Bui
(74) Attorney, Agent, or Firm—Fulwider Patton Lee & Utecht, LLP

(57) ABSTRACT

A reduced diameter stent/graft deployment catheter and a method of insertion for said catheter. The delivery sheath portion of the catheter, i.e. the distal portion of the catheter containing the stent/graft, has a larger outer diameter than the remaining proximal portion of the catheter. The reduced outer diameter of the body of the catheter allows for the use of a smaller diameter introducer sheath. The method of inserting said catheter comprises the following steps: First, the delivery sheath portion of the catheter is inserted into the patient. Next, an introducer sheath, with an outer diameter which is no larger than the outer diameter of the delivery sheath, is disposed about the catheter and its distal portion inserted into the patient. The catheter is then advanced into the patient and the stent/graft deployed.

12 Claims, 5 Drawing Sheets

REDUCED DIAMETER STENT/GRAFT DEPLOYMENT CATHETER

The captioned application is a continuation under 37 C.F.R. §1.53(b) of U.S. Ser. No. 09/006,113, filed Jan. 13, 1998 now U.S. Pat. No. 6,074,398.

BACKGROUND OF THE INVENTION

1. Field of the Invention

The invention relates to a stent/graft deployment catheter, particularly for repairing defects in arteries and other lumens within the body. More particularly, the invention relates to a reduced diameter stent/graft deployment catheter for delivering a stent/graft in situ for repairing defective body lumens, aneurysms, and particularly abdominal aortic aneurysms.

2. Description of the Prior Art

An abdominal aortic aneurysm (AAA) is a sac caused by an abnormal dilatation of the wall of the aorta as it passes through the abdomen. The aorta is the main artery of the body, supplying blood to all organs and parts of the body except the lungs. It arises from the left ventricle of the heart, passes upward, bends over and passes down through the thorax and through the abdomen, and finally divides into the iliac arteries which supply blood to the pelvis and lower extremities.

The AAA ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is bridged with a prosthetic device, such as a synthetic graft.

As with all major surgeries, there are many disadvantages to the above mentioned surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the unsuitability of the surgery for many patients, particularly older patients exhibiting comorbid conditions; and the problems associated with performing the surgical procedure on an emergency basis after the aneurysm has already ruptured.

In view of the above mentioned disadvantages of conventional surgical repair techniques, techniques have been developed for repairing AAAs by intraluminally delivering an aortic graft to the aneurysm site through the use of a catheter based delivery system, and securing the graft within the aorta using an expandable stent. Since the first documented clinical application of this technique was reported by Parodi et al. in the Annals of Vascular Surgery, Volume 5, pages 491–499 (1991), the technique has gained more widespread recognition and is being used more commonly. As vascular surgeons have become more experienced with this endovascular technique, however, certain problems have been encountered. One major problem involves the stiffness of the catheter body. Surgeons have encountered difficulty in navigating the prior art catheter through the vessel tree of a patient. Therefore, the need exists for a stent/graft deployment catheter capable of being more easily navigated through the vessel tree of a patient.

Use of the stent/graft deployment catheter eliminates the problem of suturing the graft to the aorta associated with surgical repair techniques. However, use of the catheter still requires a cut-down surgery to locate and expose the blood vessel and thus the patient recovery time is still quite long. Therefore, the need exists for a stent/graft deployment catheter which can be inserted percutaneously into the blood vessel of the patient. A percutaneous procedure would avoid the surgery necessary to locate the blood vessel and thereby decrease patient recovery time significantly. The presence of such a catheter on the market may finally allow for the full transition from the currently used surgical cut-down method of stent/graft insertion to the much preferred percutaneous insertion method. Such a catheter has not appeared on the market yet because of the difficulty inherent in designing a catheter small enough to be inserted percutaneously. The present invention does not disclose such a catheter. Rather the present invention recognizes the ever existing need for smaller catheters and therefore discloses a catheter design which can be used to decrease the diameter of any catheter on the market including eventually a catheter appropriately sized for percutaneous insertion.

Large catheters are also problematic because they require large size insertion holes which are traumatic to the blood vessel and which require surgery to repair. Therefore, the need exists for a smaller size catheter which may be inserted through a reduced diameter insertion hole in the blood vessel.

Another problem with the use of a stent/graft deployment catheter, regardless of whether it is introduced percutaneously or via the surgical cut-down method, is that its presence in the blood vessel during the stent/graft deployment procedure restricts blood flow in the blood vessel. Therefore, the need exists for a stent/graft deployment catheter which minimizes the amount of blood flow restriction during the stent/graft deployment procedure.

SUMMARY OF THE INVENTION

Accordingly, it is an object of the invention to produce a reduced diameter flexible stent/graft deployment catheter which would allow for easier navigation through often tortuous arteries and also for a smaller insertion hole in the femoral artery.

It is another object of the invention to produce a method for insertion of said reduced diameter flexible stent/graft deployment catheter.

It is still another object of the invention to produce a reduced diameter stent/graft deployment catheter which minimizes the amount of blood flow restriction in the catheter occupied blood vessel.

The invention is a reduced diameter stent/graft deployment catheter and a method of insertion for said catheter. The delivery sheath portion of the catheter, i.e. the distal portion of the catheter containing the stent/graft, has a larger outer diameter than the remaining proximal portion of the catheter. The reduced outer diameter of the body of the catheter allows for the use of a smaller diameter introducer sheath. The method of inserting said catheter comprises the following steps: First, the delivery sheath portion of the catheter is inserted into the patient. Next, an introducer sheath, with an outer diameter which is no larger than the outer diameter of the delivery sheath, is disposed about the catheter and its distal portion inserted into the patient. The catheter is then advanced into the patient and the stent/graft deployed.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
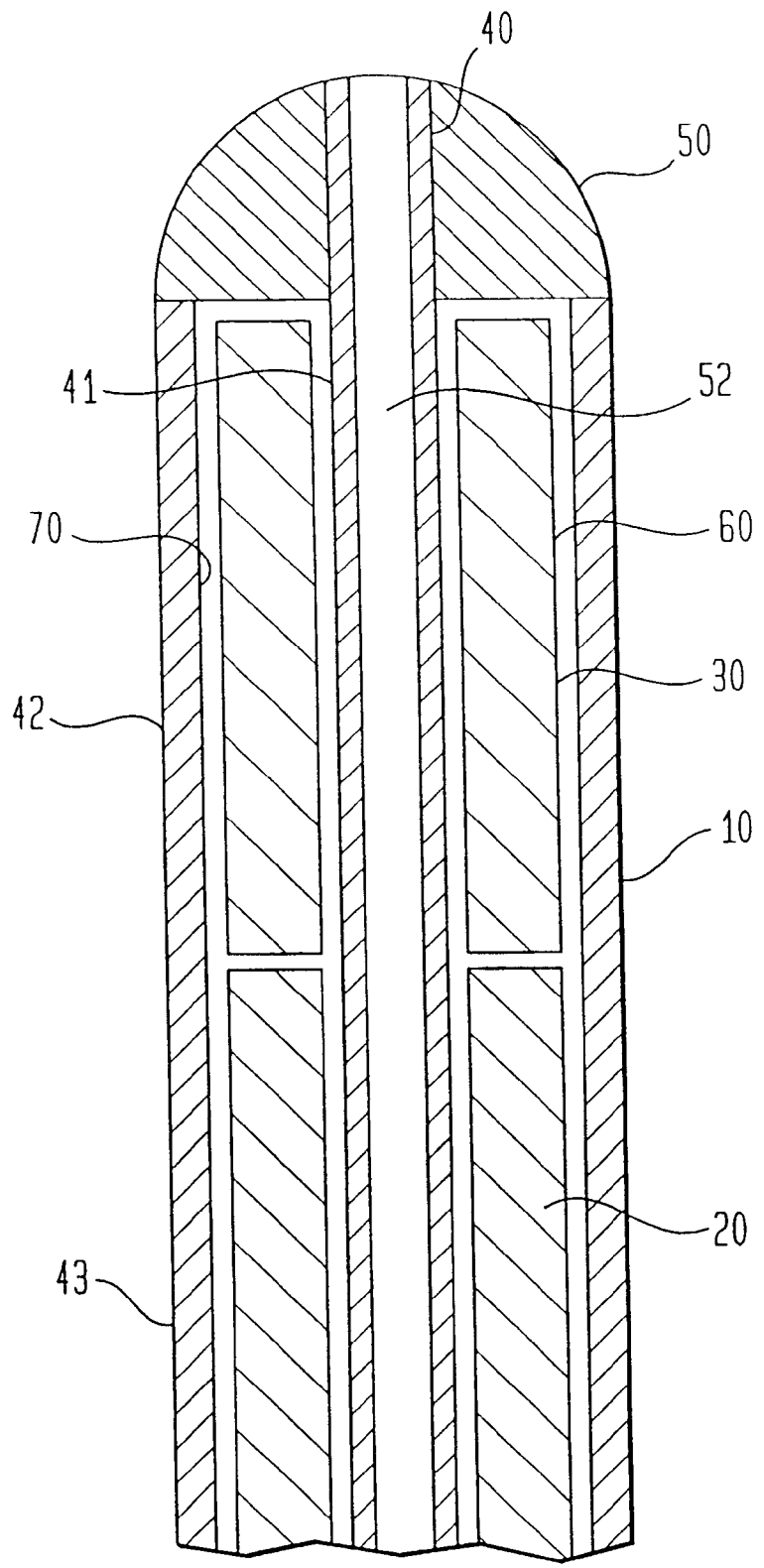
FIG. 1 is longitudinal cross section of a distal portion of a prior art stent/graft deployment catheter.

FIG. 1 illustrates a longitudinal cross section of a co-axial prior art stent/graft deployment catheter. Said catheter is comprised of a catheter body 10, a tip 50, an inner tube 40, a stent/graft 30, and a plunger 20, all of which are co-axial and have proximal and distal ends. Only the distal portion of the deployment catheter is shown for clarity. The catheter body 10 is slidingly disposed about the inner tube 40 and has a delivery sheath portion 42, a tube portion 43, and an inner surface 70. The plunger 20 is slidingly disposed about the inner tube 40 and is slidingly disposed within the catheter body 10. The distal end of the inner tube 40 is attached to the tip 50. The stent/graft 30 is slidingly disposed about the inner tube 40 and within the delivery sheath portion 42 of the catheter body 10 and is between the proximal end of the tip 50 and the distal end of the plunger 20. The stent/graft 30 has an outer surface 60 and a lumen 52 extending from its proximal end to its distal end. The stent/graft lumen 52 is occupied by a distal portion 41 of the inner tube 40. The delivery sheath portion 42 of the catheter body 10 is located between the tip 50 and the tube portion 43 of the catheter body 10. The inner and outer diameters of the delivery sheath portion 42 and the tube portion 43 are the same.

Figure 2:
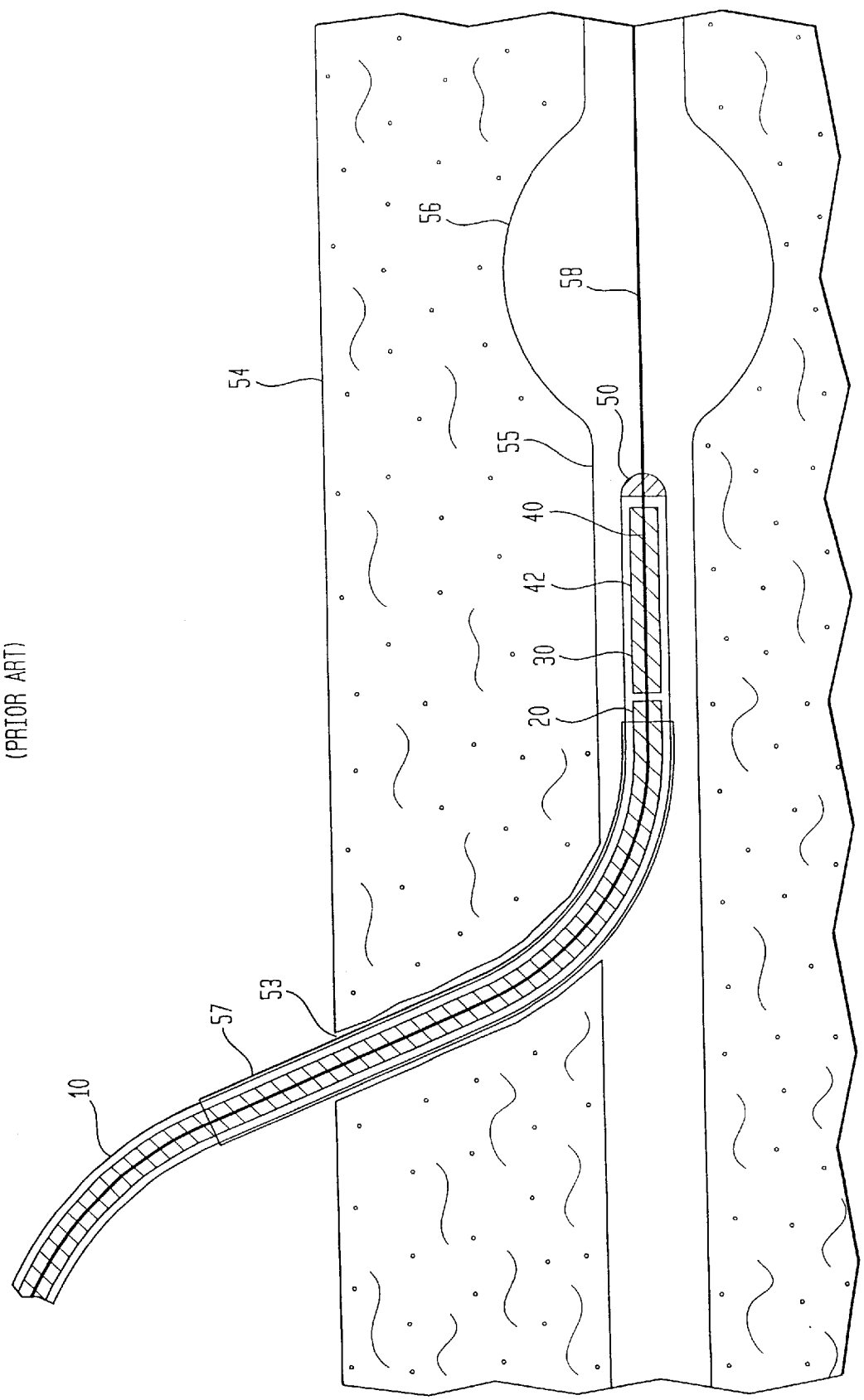
FIG. 2 illustrates a longitudinal cross section of the prior art catheter of FIG. 1 percutaneously inserted into a patient's blood vessel.

The stent/graft deployment catheter may be inserted percutaneously or via a surgical cut-down method into a blood vessel. FIG. 2 illustrates a longitudinal cross section of the prior art catheter percutaneously inserted in a blood vessel 55 of a patient 54. The delivery sheath portion 42 of the catheter is still down stream of an aneurysm 56 in need of repair and has fully exited an introducer sheath 57. If inserted percutaneously, as illustrated in FIG. 2, a guide wire 58 is first advanced through an insertion site 53 into the blood vessel 55 of the patient 54. Next, a dilator sheath assembly (dilator not shown) is disposed about the guide wire 58 and the distal portion of the dilator is used to dilate the insertion site 53. After dilation of the insertion site 53 the dilator is removed while the insertion sheath 57 is held in place in the blood vessel 55 of the patient 54. Next, the catheter is inserted into the introducer sheath 57 and is advanced forward into the blood vessel 55 of the patient 54.

Upon proper positioning of the tip 50 in the blood vessel 55 the plunger 20 is held in place while the catheter body 10 is pulled away from the tip 50 exposing the entire stent/graft 30 to blood. Upon contact with blood the stent/graft 30 expands such that the diameter of the stent/graft lumen 52 becomes larger than the outer diameter of the tip 50. The expanded stent/graft 30 becomes fixed in place in the blood vessel 55 and thus bridges the aneurysm. The inner tube 40 is then pulled away from the stent/graft 30 such that the tip 50 passes through the stent/graft lumen 52. Finally, the catheter is removed from the patient 54. Note that there are many other types of self-expandable stent/grafts on the market including heat sensitive and spring-like stent/grafts. Note further that one major function of the introducer sheath 57 is to control bleeding at the insertion site 53 of the patient 54 during the entire procedure.

Figure 3:
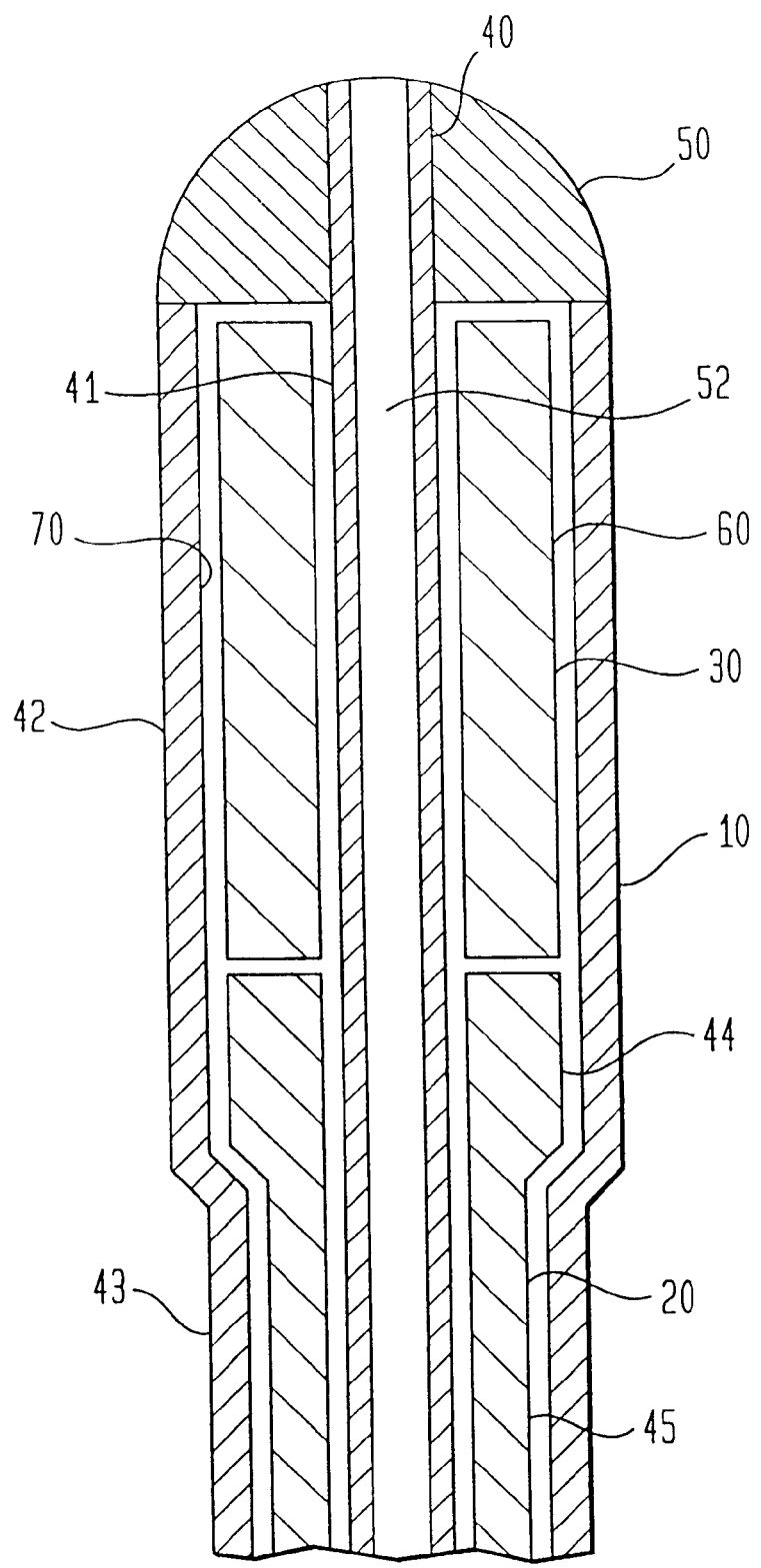
FIG. 3 is longitudinal cross section of a distal portion of an improved reduced diameter stent/graft deployment catheter.

FIG. 3 illustrates a longitudinal cross section of an improved reduced diameter stent/graft deployment catheter. Said catheter is comprised of a catheter body 10, a tip 50, an inner tube 40, a stent/graft 30, and a plunger 20, all of which are co-axial and have proximal and distal ends. Only the distal portion of the deployment catheter is shown for clarity. The catheter body 10 is slidingly disposed about the inner tube 40 and has a delivery sheath portion 42, a tube portion 43, and an inner surface 70. The plunger 20 is slidingly disposed about the inner tube 40 and slidingly disposed within the catheter body 10. The distal end of the inner tube 40 is attached to the tip 50. The stent/graft 30 is slidingly disposed about the inner tube 40 and within the delivery sheath portion 42 of the catheter body 10 and is located between the tip 50 and the distal end of the plunger 20. The stent/graft 30 has an outer surface 60 and a lumen 52 extending from its proximal end to its distal end. The stent/graft lumen 52 is occupied by a distal portion 41 of the inner tube 40. The delivery sheath portion 42 of the catheter body 10 is located between the tip 50 and the tube portion 43 of the catheter body 10. The outer and inner diameters of the tube portion 43 of the catheter body 10 are smaller than the outer and inner diameters of the delivery sheath portion 42 of the catheter body 10, respectively. The plunger 20 has a delivery sheath portion 44 and a tube portion 45.

Figure 4:
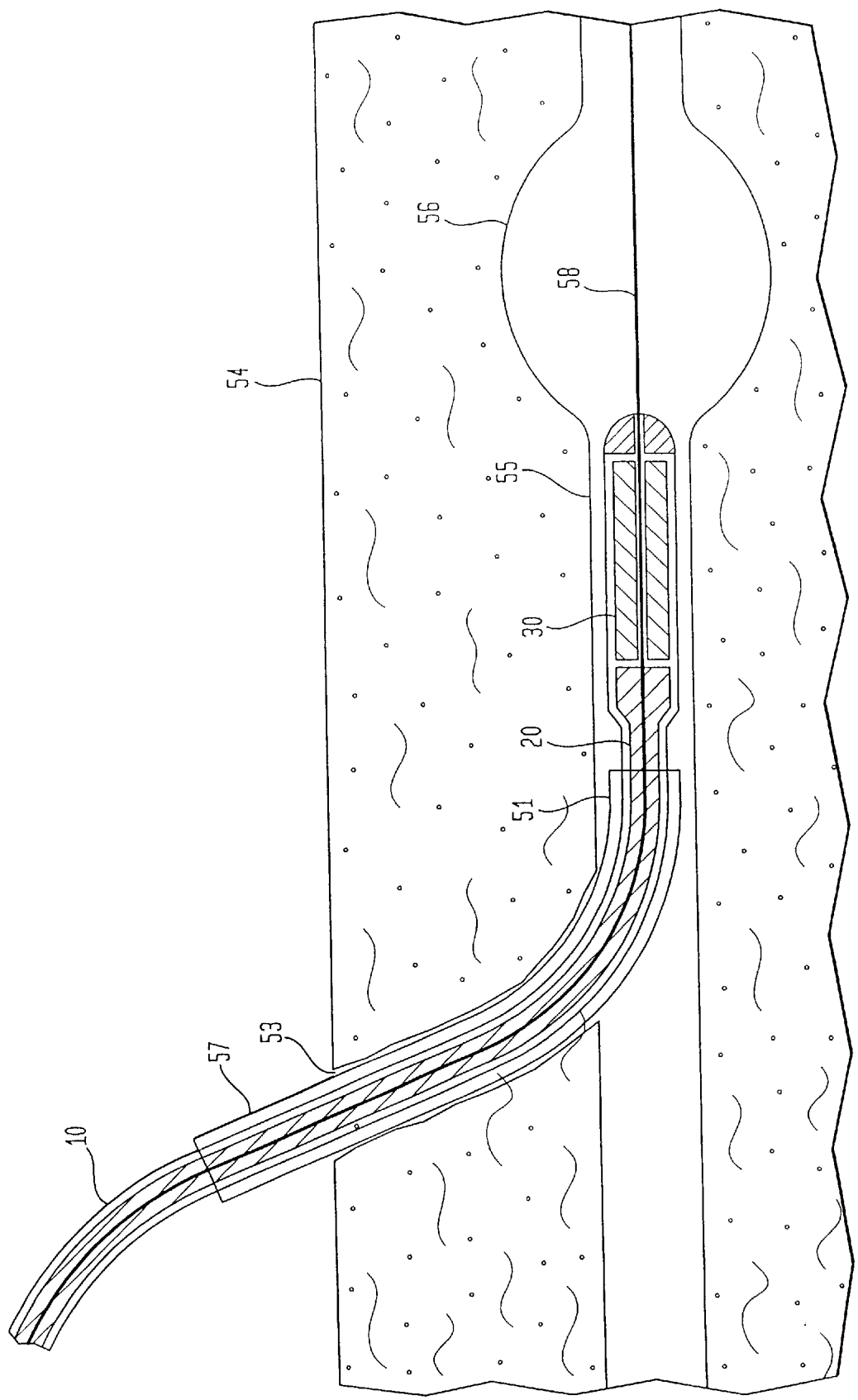
FIG. 4 illustrates a longitudinal cross section of the inserted improved catheter of FIG. 3 after the insertion sheath has been inserted into the patient.
Figure 5:
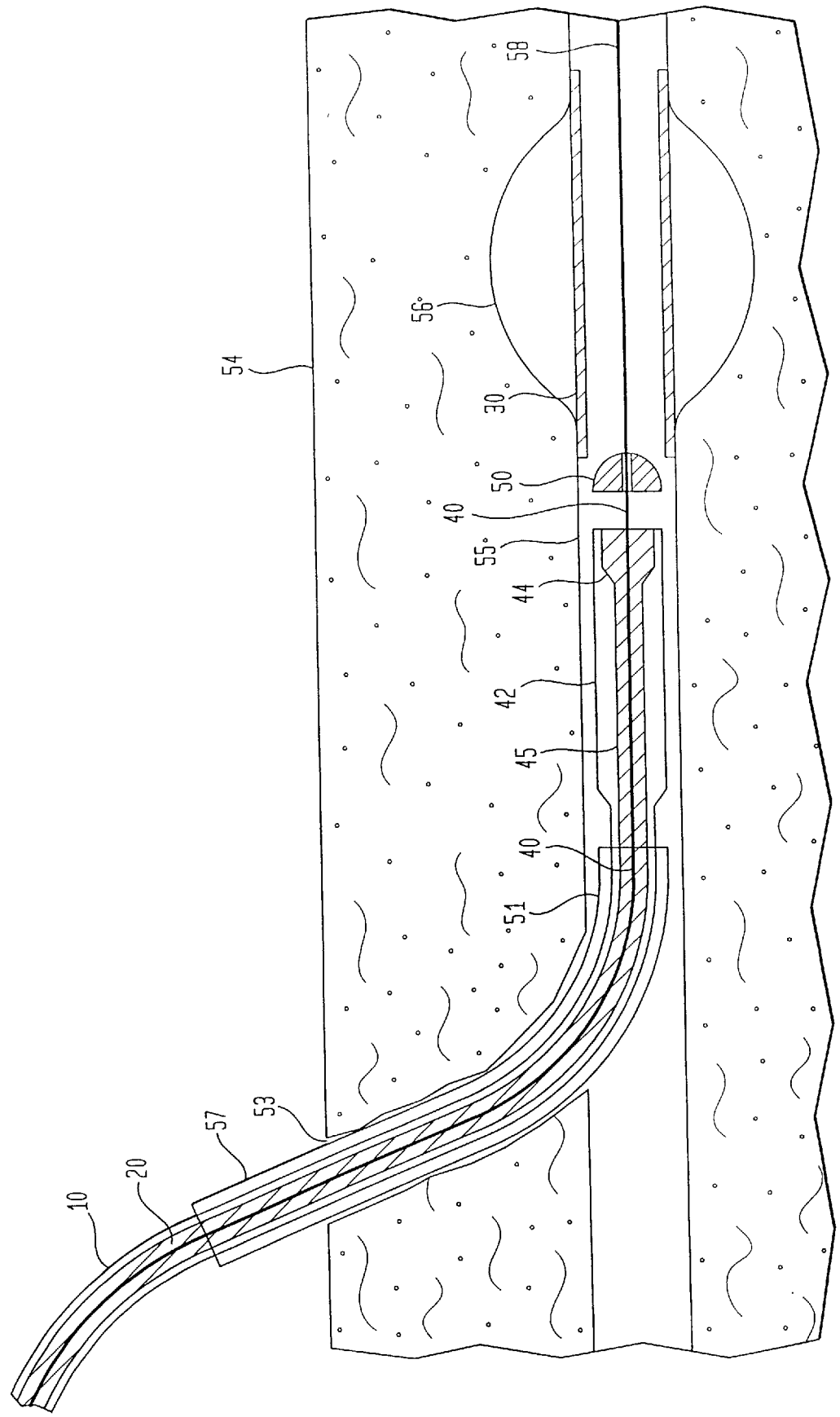
FIG. 5 illustrates a longitudinal cross section of the inserted improved reduced diameter catheter of FIG. 3 after the stent/graft has expanded and the tip has been pulled through the stent/graft lumen.

Similar to the prior art catheters, the reduced diameter stent/graft deployment catheter may be inserted percutaneously or via a surgical cut-down method into a blood vessel. FIG. 4 illustrates a longitudinal cross section of a reduced diameter introducer sheath 57 and an improved reduced diameter stent/graft deployment catheter percutaneously inserted in a blood vessel 55 of a patient 54. The delivery sheath portion 42 of the catheter is still down stream of an aneurysm 56 in need of repair and is inserted before an introducer sheath 57. If inserted percutaneously, as illustrated in FIG. 4, a guide wire 58 is first advanced through an insertion site 53 into the blood vessel 55 of the patient 54. Next, a dilator (not shown) is disposed about the guide wire 58 and its distal portion is used to dilate the insertion site 53. After removal of the dilator the catheter is disposed about the guide wire 58 and is advanced into the blood vessel 55 such that the entire delivery sheath portion 42 is enveloped by the blood vessel 55. The reduced diameter introducer sheath 57 is then disposed about the tube portion 43 of the catheter body 10 and is advanced forward such that its distal portion 51 is inserted into the blood vessel 55. The outer diameter of the introducer sheath 57 is about the same as the outer diameter of the delivery sheath portion 42 of the catheter body 10. Thus inserting the delivery sheath portion 42 into the blood vessel 55 first, before inserting the introducer sheath 57, allows for the use of a smaller introducer sheath. The introducer sheath 57 must be large enough only to accommodate the tube portion 43 of the catheter body 10. Next, the catheter is advanced forward into the blood vessel 55 of the patient 54. Upon proper positioning of the tip 50 in the blood vessel 55 the plunger 20 is held in place while the catheter body 10 is pulled back away from the tip 50 exposing the entire stent/graft 30 to blood. Upon contact with the patient's blood the stent/graft 30 expands such that the diameter of the stent/graft lumen 52 is larger than the outer diameter of the tip 50. The expanded stent/graft 30 becomes fixed in place in the blood vessel 55 and thus bridges the aneurysm. Next, the inner tube 40 is pulled away from the stent/graft 30 such that the tip 50 passes through the stent/graft lumen 52. FIG. 5 illustrates a longitudinal cross section of the inserted improved reduced diameter catheter after the stent/graft 30 has expanded and the tip 50 has been pulled through the stent/graft lumen 52. Finally, the introducer sheath 57 and then deployment catheter is removed from the patient 54.

What is claimed is:

1. A system for deploying a device within vasculature, comprising:

a catheter body, the catheter body having a sheath portion, a tube portion, a distal end and including an inner surface, the catheter body further comprises a sheath portion having a cross-sectional profile and a tube portion having a cross-sectional profile, the cross-sectional profile of said sheath portion is greater than the cross-sectional profile of said tube portion;

an inner tube slidably disposed in the catheter body; and a plunger slidably disposed in the catheter body, the plunger having a profile configured to substantially mate with the inner surface of the catheter body, the plunger further comprises a delivery sheath portion having a cross-sectional profile and a tube portion having a cross-sectional profile, the cross-sectional profile of said delivery sheath portion is greater than the cross-sectional profile of said tube portion;

wherein the inner tube is adapted to translate longitudinally independently of the plunger beyond the distal end of the catheter body.

2. The system of claim 1, wherein the delivery sheath portion has a first end portion, the first end portion having a generally frustoconical profile.

3. The system of claim 1, further comprising the tip, the tip being affixed to the inner tube.

4. The system of claim 3, wherein the tip has a generally semi-spherical profile.

5. The system of claim 1, wherein the tip is adapted to mate with the catheter body.

6. The system of claim 1, wherein the inner tube is adapted to slidably receive a guidewire.

7. The system of claim 1, wherein the inner tube is coaxially disposed within the catheter body.

8. The system of claim 1, wherein the inner tube is coaxially disposed within the plunger.

9. The system of claim 8, wherein the plunger is coaxially disposed within the catheter body.

10. The system of claim 1, wherein the catheter body, inner tube and plunger define a space for receiving a device.

11. The system of claim 1, wherein the catheter body is configured to move longitudinally with respect to the plunger.

12. The system of claim 1, wherein the inner surface of the catheter body is configured to retain an expandable device in a compressed condition.

* * * * *